United States Patent [19]
Bartelt et al.

[11] Patent Number: 5,117,826
[45] Date of Patent: Jun. 2, 1992

[54] COMBINED NERVE FIBER AND BODY TISSUE STIMULATION APPARATUS AND METHOD

[75] Inventors: James T. Bartelt, Longmont; Frank W. Harris, Boulder, both of Colo.

[73] Assignee: Staodyn, Inc., Longmont, Colo.

[21] Appl. No.: 696,987

[22] Filed: May 2, 1991

Related U.S. Application Data

[63] Continuation of Ser. No. 325,897, Mar. 20, 1989, abandoned, which is a continuation-in-part of Ser. No. 9,760, Feb. 2, 1987, Pat. No. 4,813,418.

[51] Int. Cl.⁵ .............................................. A61N 1/36
[52] U.S. Cl. ..................................... 128/421; 128/422
[58] Field of Search ............. 128/419 R, 420 R, 421, 128/422, 423

[56] References Cited

U.S. PATENT DOCUMENTS

| | | |
|---|---|---|
| 2,375,575 | 5/1945 | Morland et al. |
| 3,888,261 | 6/1975 | Maurer ................................ 128/421 |
| 3,946,745 | 3/1976 | Hsiang-Lai et al. ................. 128/421 |
| 4,237,899 | 12/1980 | Hagfors et al. ..................... 128/422 |
| 4,256,116 | 3/1981 | Meretsky et al. ................... 128/421 |
| 4,456,012 | 6/1984 | Lattin ................................ 128/420 R |
| 4,640,286 | 2/1987 | Thomson ............................ 128/421 |
| 4,664,118 | 5/1987 | Batters ............................... 128/421 |
| 4,759,368 | 7/1988 | Spanton et al. .................... 128/421 |
| 4,803,988 | 2/1989 | Thomson ............................ 128/421 |
| 4,846,181 | 7/1989 | Miller ................................ 128/421 |
| 4,895,154 | 1/1990 | Bartelt et al. ...................... 128/421 |
| 4,913,148 | 4/1990 | Diethelm ............................ 128/421 |
| 4,926,865 | 5/1990 | Oman ................................. 128/421 |

*Primary Examiner*—Ruth S. Smith
*Attorney, Agent, or Firm*—Robert E. Harris

[57] ABSTRACT

An electronic device and method are disclosed for effecting both nerve fiber and body tissue stimulation. Nerve fiber stimulation is primarily effected by application of pulses, and preferably by application of biphasic pulse pairs the pulses of which are spaced from one another in a pattern such that nerve fiber stimulation applied through plural active electrodes enhances pain suppression. Body tissue treatment is primarily effected by application of a net DC charge, and preferably by application of biphasic pulses that includes a greater number of either negative or positive pulses so that a net DC charge results. The DC charge level is maintained at a substantially constant selected value regardless of pulse variations within established broad limits, and the DC charge level is adjustable between operational modes, as needed.

19 Claims, 10 Drawing Sheets

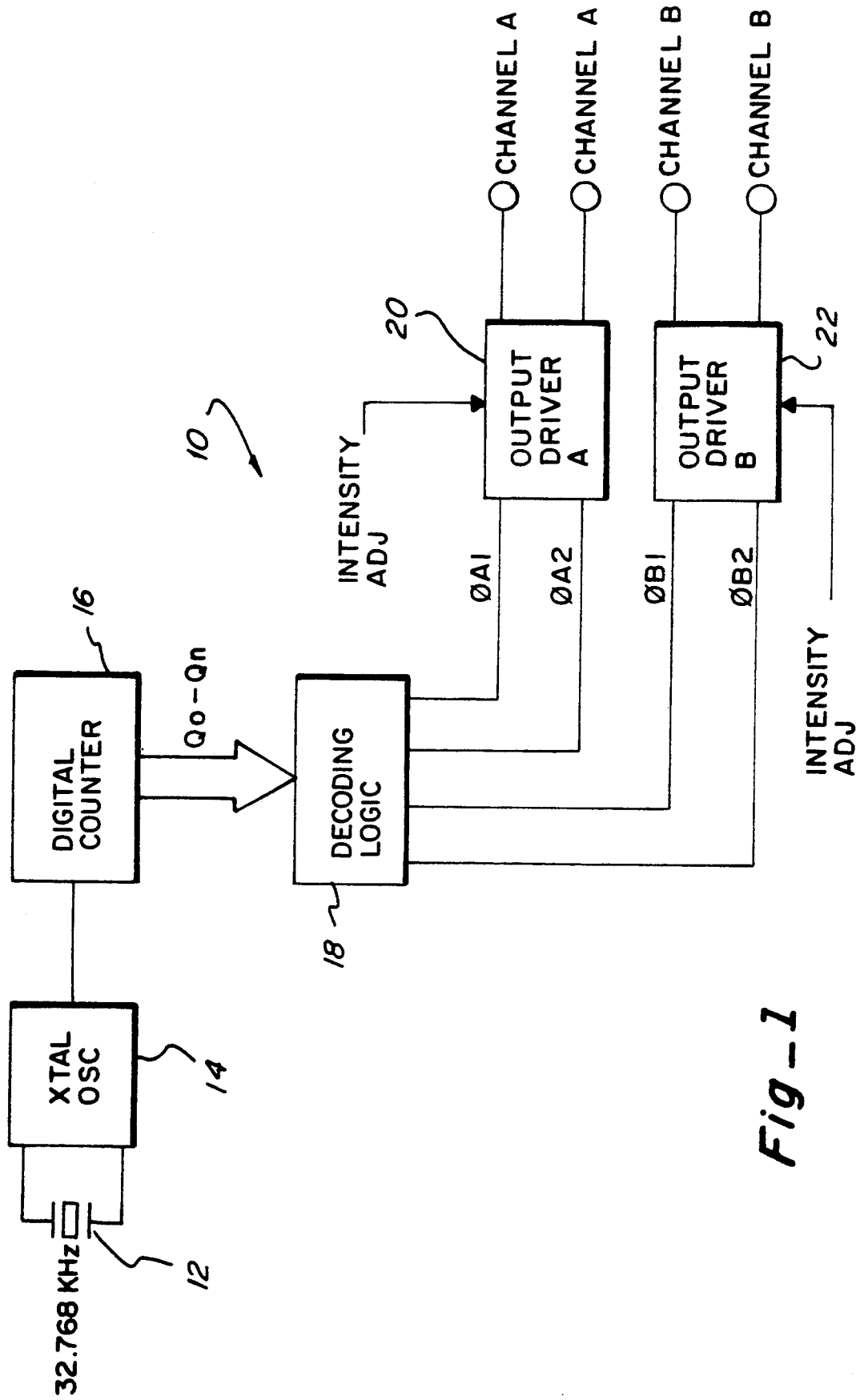
Fig_1

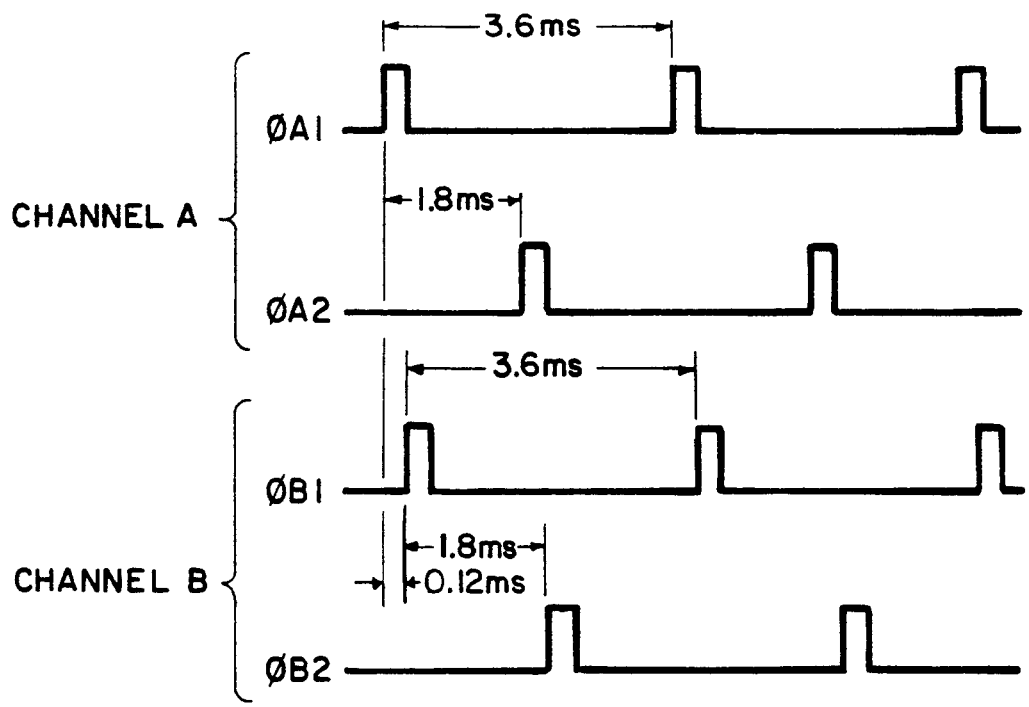
Fig_2
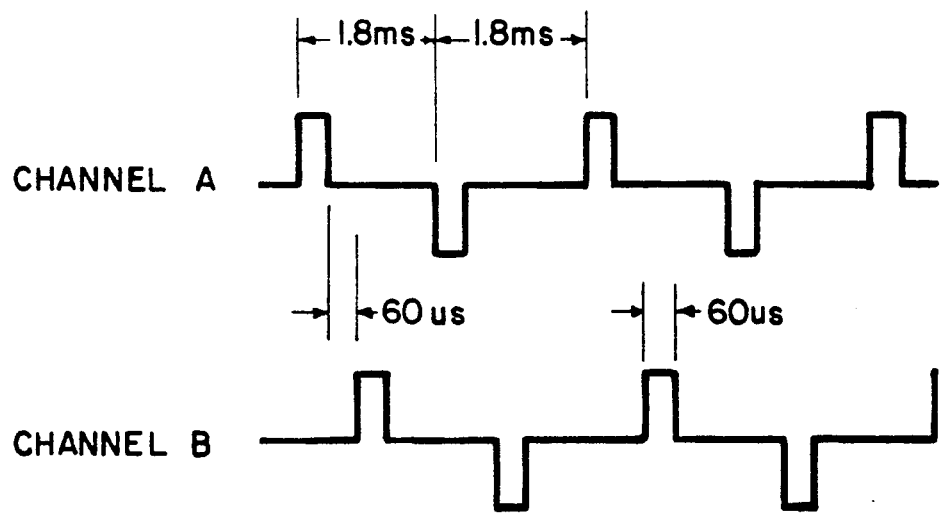
Fig_3

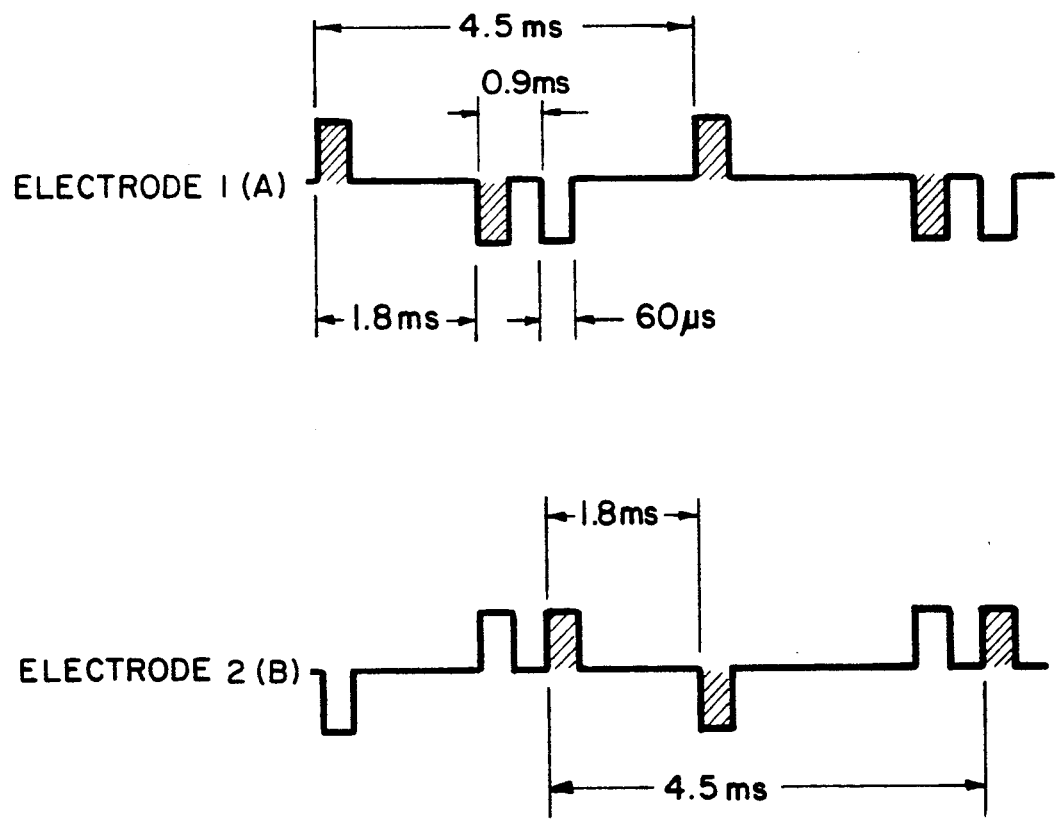
*Fig_4*
PRIOR ART

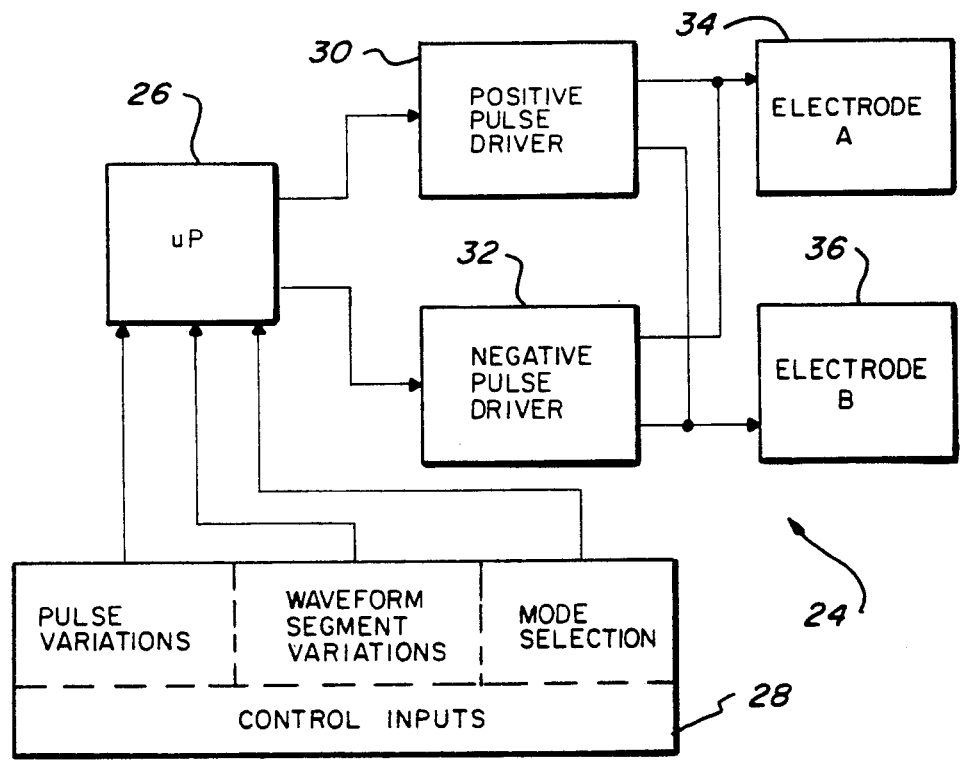
Fig_5
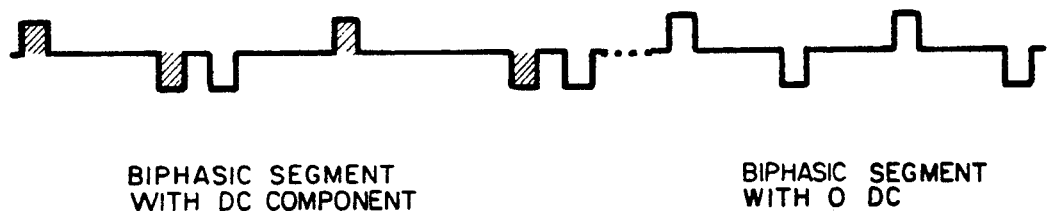
BIPHASIC SEGMENT
WITH DC COMPONENT
BIPHASIC SEGMENT
WITH 0 DC
Fig_6

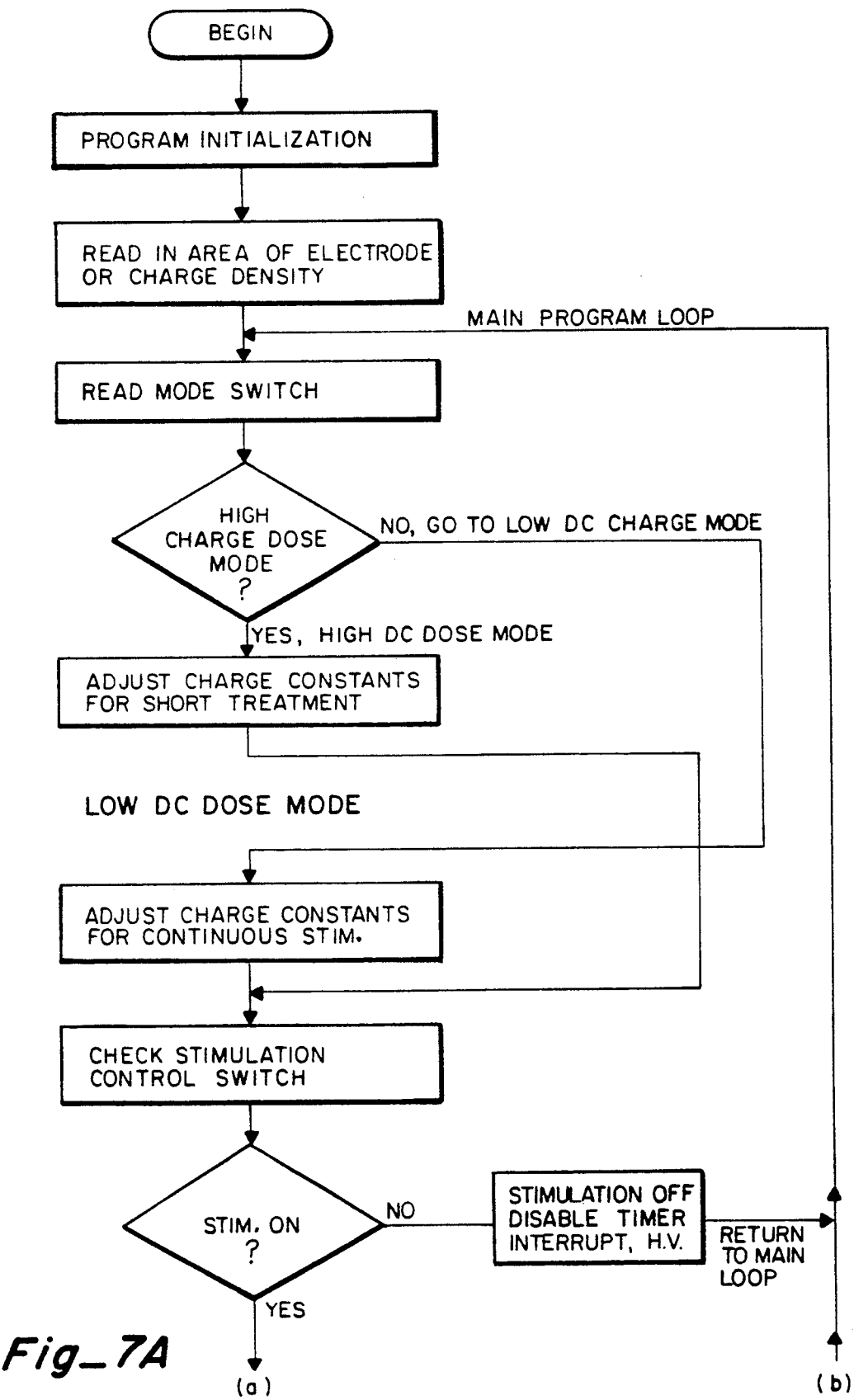
Fig_7A

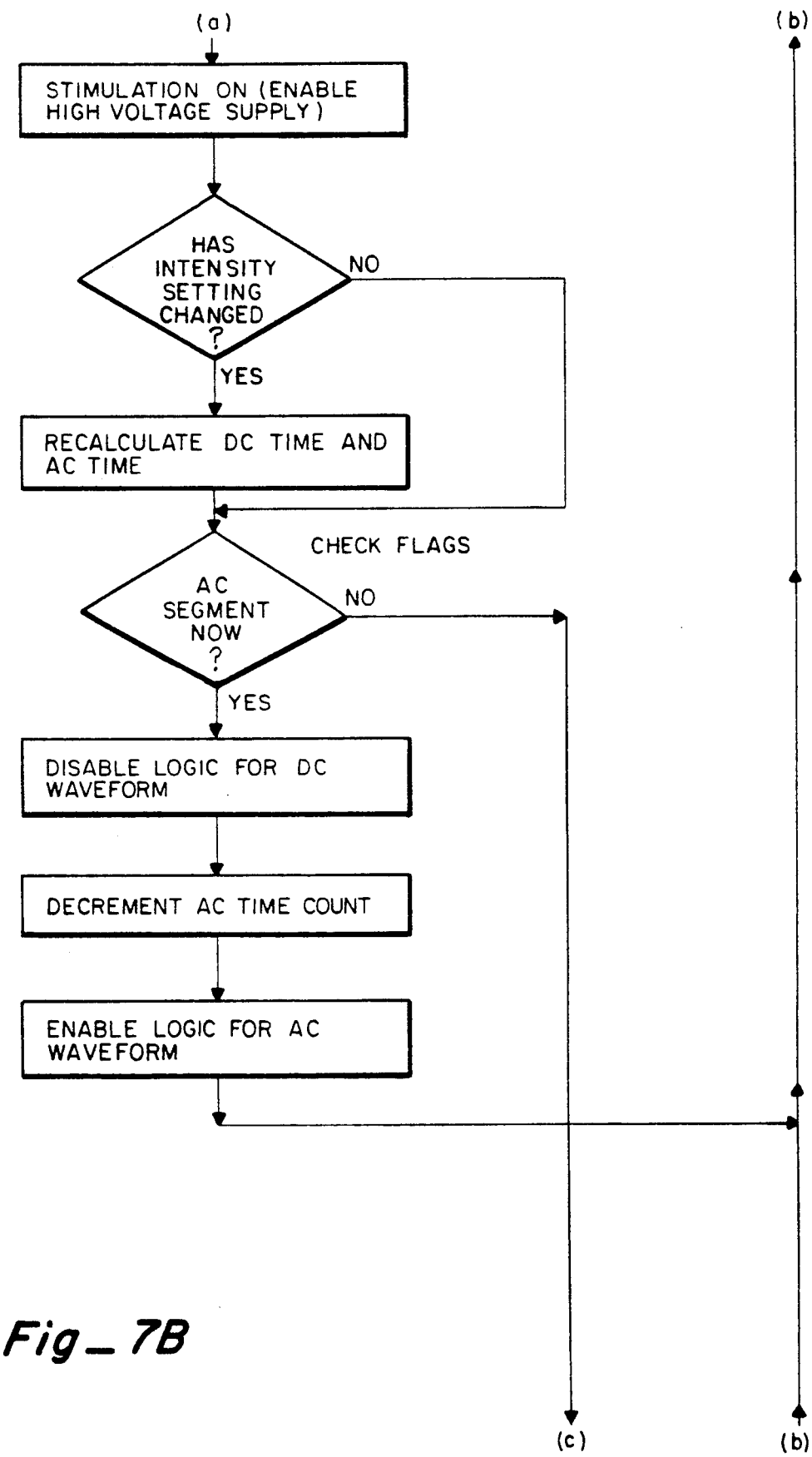
Fig_7B

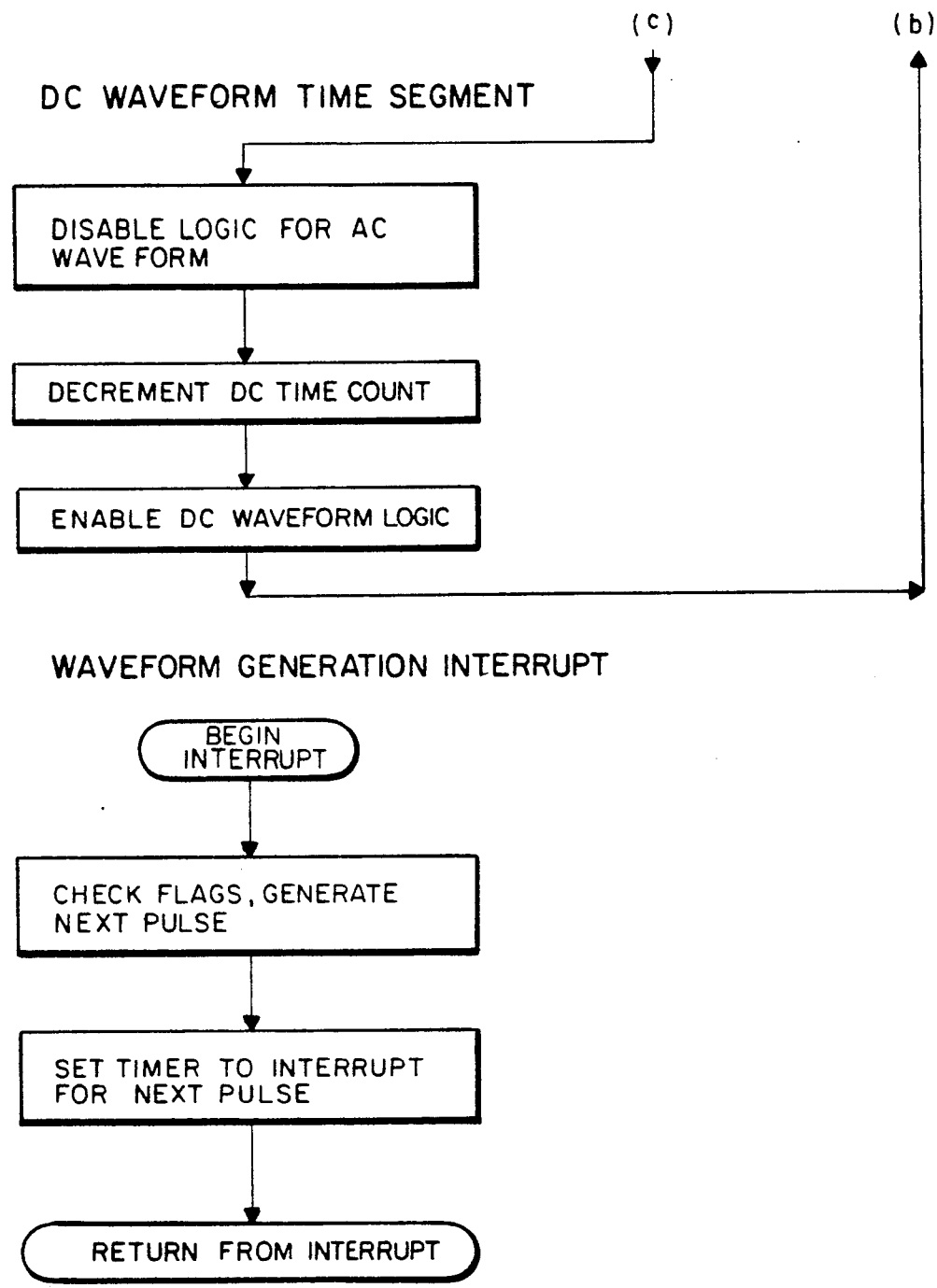
Fig_7C

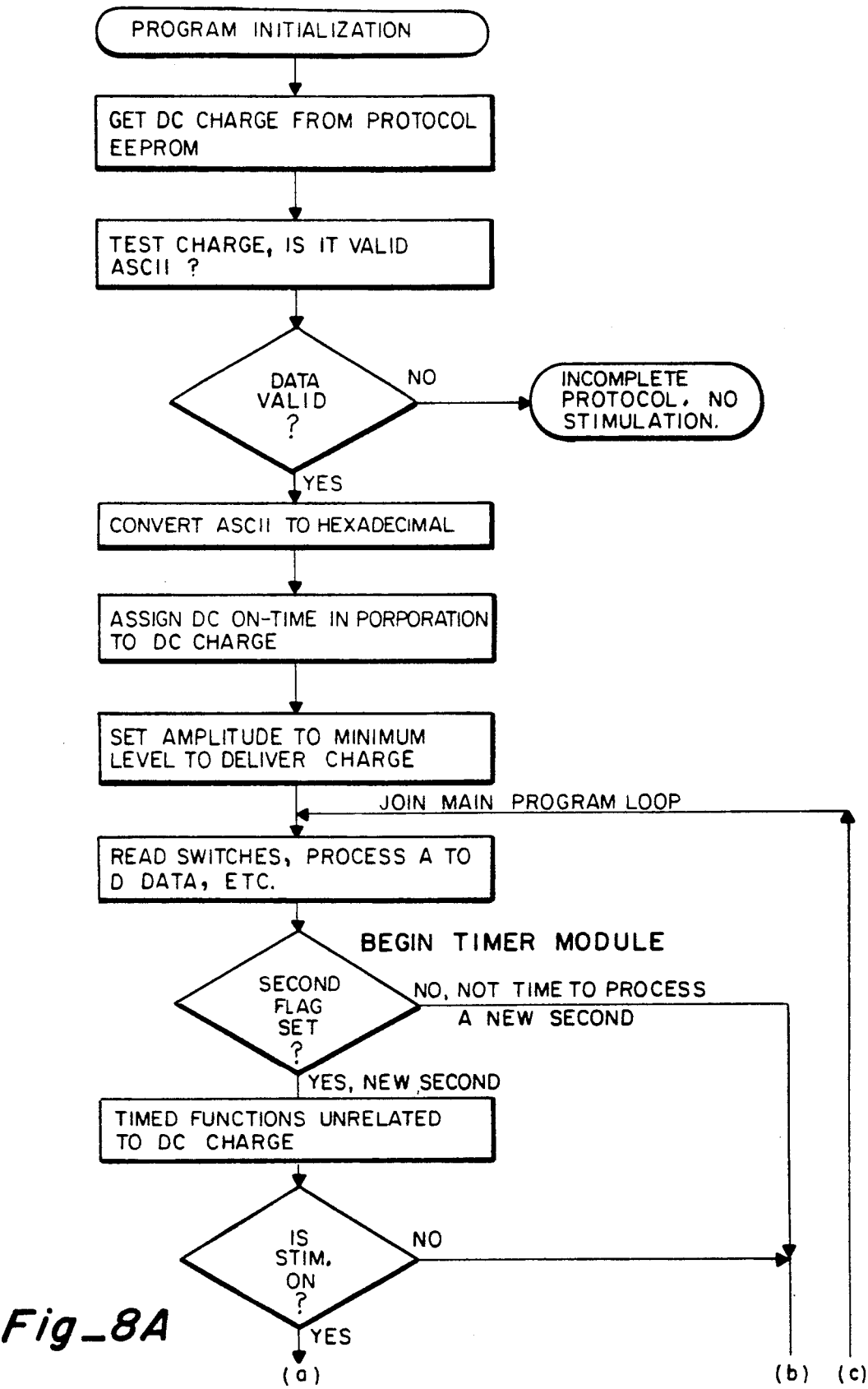
Fig_8A

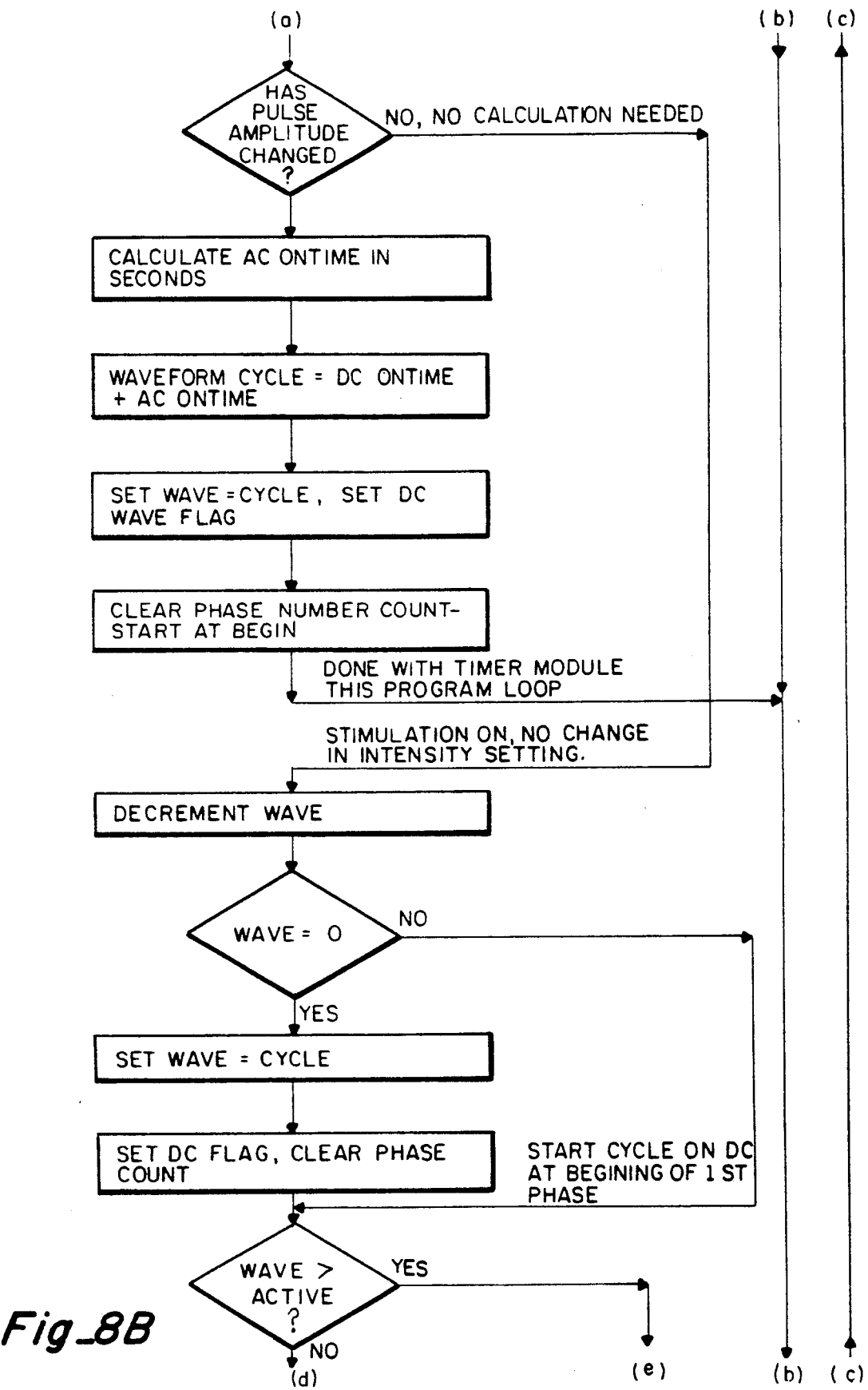
Fig_8B

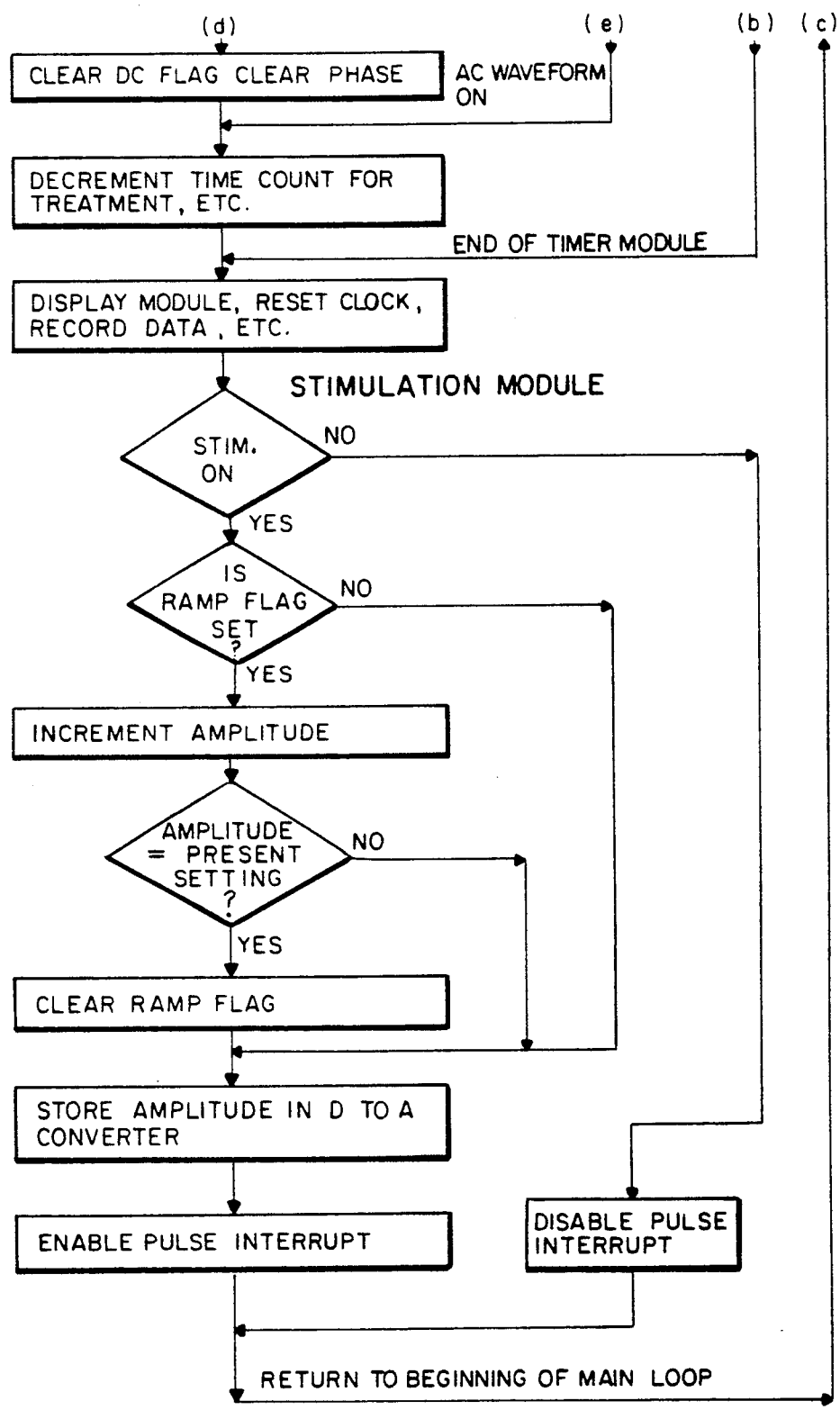
Fig_8C

COMBINED NERVE FIBER AND BODY TISSUE STIMULATION APPARATUS AND METHOD

RELATED INVENTION

This application of a continuation of application Ser. No. 07/325,897, filed Mar. 20, 1989 now abandoned, which application was is a continuation-in-part of U.S. Pat. Application Ser. No. 07/009,760 filed Feb. 2, 1987 by Frank W. Harris and entitled "NERVE FIBER STIMULATION USING SYMMETRICAL BIPHASIC WAVEFORM APPLIED THROUGH PLURAL EQUALLY ACTIVE ELECTRODES" issued Mar. 21, 1988 as U.S. Pat. No. 4,813,418.

FIELD OF THE INVENTION

This invention relates to electrical stimulation and treatment of the body, and, more particularly, relates to nerve fiber and body tissue stimulation to effect pain suppression and wound treatment.

BACKGROUND OF THE INVENTION

It has heretofore been common to electrically stimulate nerve fibers for various therapeutic purposes, and medical practitioners have heretofore used electrical signals for various other purposes, including, for example, stimulation of muscle activity and producing of various sensations.

The sequence of effects produced by electrical stimulation, as its intensity is increased, is known to generally follow a pattern of a perception of electrical sensation (usually tingling), an increase in sensation, fasciculation muscle contraction, pain, and then more severe demonstrative effects such as electrical burns or cardiac arrhythmias.

While therapeutic effects often occur while stimulation is applied with a continuous intensity below that necessary to produce muscle contraction, exceptions do occur in the general effect pattern such as, for example, when a steady DC current is applied in slowly increased intensity, muscle contraction cannot be obtained, though the sequence of effects occur in the same order, and, for example, in a DC overdose situation, electrical burns can occur.

Electrical stimulation has been attempted and/or realized through use of a wide variety of electrical waveforms and these waveforms have ranged from purely DC (galvanic) current or voltage to many different combinations of electrical pulses of various shapes and durations. While at least some such waveforms have provided some degree of desirable effect, the results achieved have been random with no clear understanding of how such waveforms might be combined and/or grouped to enhance results.

As mentioned above, stimulation has been made to occur with many different types of pulses, and use of pulse pairs that include both positive and negative pulses have heretofore been suggested (see, for example, U.S. Pat. Nos. 2,375,575, 3,946,745, 4,237,899, and 4,256,116).

While these patents suggest that biphased pulsed pairs can be utilized for therapeutic purposes, there is no apparent teaching in these patents of combining different types of biphased pulses to achieve dual ends.

Apparatus and method directed to optimizing stimulation using biphasic pulses is shown and claimed in U.S. Pat. No. 4,640,286, entitled "OPTIMIZED NERVE FIBER STIMULATION" issued Feb. 3, 1987 to Thomas H. Thomson, and in U.S. Pat. No. 4,803,988, entitled "NERVE FIBER STIMULATION USING PLURAL EQUALLY ACTIVE ELECTRODES" issued Feb. 14, 1989 to Thomas H. Thomson, both of which patents are assigned by the assignee of this invention. Nerve fiber stimulation using biphasic pulses in a symmetrical pattern is shown and claimed in U.S. Pat. Application Ser. No. 07/009,760, issued Mar. 26, 1989 as U.S. Pat. No. 4,813,418, which application is the parent application of this application as stated above.

It has also been heretofore suggested that edema can be reduced and wound healing can be enhanced by application of negative DC to a wound. Application of negative pulses to a wound (as well as application of positive pulses and combinations of alternately positive and negative waveforms) to effect wound healing is shown in U.S. Pat. Application Ser. No. 07/103,696 filed Oct. 2, 1987 by Katherine H. Miller, entitled "SOFT TISSUE WOUND HEALING THERAPY UTILIZING PULSED ELECTRICAL STIMULATION", issued July 11, 1989 as U.S. Pat. No. ,846,181, and assigned to the assignee of this invention.

SUMMARY OF THE INVENTION

This invention provides apparatus and method for effecting both nerve fiber stimulation (to suppress pain) and body tissue stimulation (to treat the body such as by promoting healing of wounds and/or reduction of edema). Nerve fiber stimulation can be effected by application of AC and is preferably effected through application of biphasic pulse pairs having the pulses spaced from one another in a pattern that enhances nerve fiber stimulation, while body treatment can be effected by application of DC, and is preferably effected by a net DC charge resulting from application of biphasic pulses having a greater number of pulses of one polarity.

In the now preferred embodiment of this invention, a combined waveform having two segments, one of which segments includes biphasic pulses have a greater number of negative pulses, provided in a manner such as shown in U.S. Pat. No. 4,803,988, to provide a net negative DC charge, and the other of which segments includes biphasic pulse pairs, arranged in a symmetrical pattern, to provide substantially zero DC charge.

By controlling the time duration of application of the net DC charge relative to that of the pulse waveform providing no DC charge, the DC charge can be maintained constant regardless of pulse variations due to changes in intensity (and/or other parameters such as repetition) within established limits.

In addition, by providing different modes of operation, a large DC charge can be delivered during one mode of operation, and then, by applying DC charge as needed at a controlled rate, the DC charge level can be maintained in the tissue during a second mode of operation.

It is therefore an object of this invention to provide improved apparatus and method for effecting nerve fiber and body tissue stimulation.

It is another object of this invention to provide improved apparatus and method for effecting both pain suppression and body treatment using electrical stimulation.

It is another object of this invention to provide improved apparatus and method for effecting nerve fiber and body tissue stimulation utilizing a combination of different pulse waveforms.

It is still another object of this invention to provide improved apparatus and method for effecting nerve fiber and body tissue stimulation utilizing a first pulse waveform supplying a net DC charge and a second pulse waveform supplying substantially zero DC charge.

It is still another object of this invention to provide improved apparatus and method for effecting nerve fiber and body tissue stimulation utilizing a first signal segment supplying a DC charge and a second signal segment supplying substantially zero DC charge with the resulting DC charge being maintained substantially constant regardless of variations, within establishable limits, in said segments.

It is yet another object of this invention to provide an improved apparatus and method for effecting nerve fiber and body tissue stimulation utilizing biphasic pulse waveforms a first segment of which applies a net DC charge and a second segment of which supplies substantially zero DC charge, with the DC charge being maintained constant regardless of variations in the pulses of the second segment.

It is yet another object of this invention to provide an improved apparatus and method for effecting nerve fiber and body tissue stimulation utilizing dual modes of operation wherein a large net DC charge is applied during one mode and maintained in the tissue during a second mode by application of a small net DC charge.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiments of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1 is a block diagram of apparatus providing a symmetrical biphasic waveform applied through plural active electrodes;

FIG. 2 is a typical representation of phased pulsed outputs useful for generating the biphasic waveform for the apparatus shown in FIG. 1;

FIG. 3 is a typical representation of the biphasic waveform produced by the apparatus of FIG. 1 showing timewise spaced pulses applied to dual channels;

FIG. 4 is a typical representation of the biphasic waveform produced by apparatus shown in U.S. Pat. No. 4,803,988 showing timewise spaced pulses applied to dual channels;

FIG. 5 is a block diagram of apparatus useful for providing a combined output according to this invention;

FIG. 6 is a typical representation of a combined waveform produced by the apparatus of FIG. 5;

FIGS. 7A, 7B, and 7C provide a flow chart illustrating use of the apparatus for post-surgical (post-op) purposes; and FIGS. 8A, 8B, and 8C provide a flow chart illustrating use of the apparatus of this invention for wound healing purposes.

DESCRIPTION OF THE INVENTION

It has been found that pain that would ordinarily be experienced by a person can often be effectively suppressed and therefore not experienced by that person if nerve fibers carrying the pain sensation toward the brain can be adequately stimulated by application of electrical current to the body of the person. It has also been found that such stimulation can be enhanced and therefore made more effective through utilization of apparatus and method developed with an understanding of the nature and function of nerve fibers.

Individual nerve cells are called neurons and are contained in cable-like bundles in the nervous tissue called nerves. The individual nerve fibers comprise a portion of a nerve cell extending from the nerve cell body to its end point where the activity for which that neuron is responsible is either detected by the neuron or influenced by the neuron. In peripheral nerves (i.e., those not contained in the spine or skull or in the autonomic nervous system), nerve fibers extend from the spinal cord as a continuous filament to the point where they interact with other tissue.

Nerve fibers conduct information in much the same manner as does a cable, and generally carry information in binary form. The number of nerve pulses per unit time determines the degree of activity since each nerve pulse for a given nerve fiber is identical (for practical purposes) to every other pulse relayed by that fiber.

The electrical activity of nerve fibers can be generalized, for purposes as follows:

Action Potential is the firing of the neuron caused by either natural or artificial stimulation of the nerve;

Absolute Refractory Period is a period of time when the nerve cannot be caused to fire (i.e., to produce a second pulse), regardless of how strongly it is stimulated, and this period of time sets the upper limit on the frequency or the rate that the neuron can fire; and Relative Refractory Period is a period of time wherein a stronger than normal stimulus is required to fire, or excite, the nerve, with the strength or intensity of the stimulus required to stimulate the nerve fiber diminishing over time until it reaches a minimum when the fiber has reached its resting potential, and the relative refractory period can contribute to setting the upper limit of the expectation (firing) rate of the neuron, depending upon stimulus intensity.

Neurons may be classified by their fiber diameters and the activity for which they are responsible. When so classified, a number of basic groups are formed (six basic groups are commonly noted, but other groupings are also occasionally noted), including fiber class C (pain and autonomic). The time length which the neuron remains within the various periods mentioned are different for each class of neurons. For fiber class C (pain and autonomic) the fibers have a size diameter of <1.3 micrometers, a conduction velocity (CV) of 0.7 to 2.3 meter per second, a refractory period (RP) of 1.8 milliseconds, and a hyperexcitability time (HE) of 4.5 milliseconds.

Nerves contain a mixture of fibers with large numbers of each type of fiber (including class C fibers) being normally included in the nerve. The effect of electrical stimulation is increased by increasing the frequency with which the stimulus is able to fire the individual fibers (as noted previously) as well as increasing the total number of individual fibers of the same class which are excited simultaneously.

For a more complete explanation of the foregoing, the following references can be utilized: Roger Warwick and Peter L. Williams, GRAY'S ANATOMY, 35th British Edition (Philadelphia: W.B. Saunders Company), multiple citations; Verrnon B. Mountcastle, MEDICAL PHYSIOLOGY, 14th ed. (St. Louis, Toronto, London: The C.V. Mosby Company), vol 1 and 2, multiple citations; Percival P. Newman, NEUROPHYSIOLOGY, (New York: SP Medical & Scientific Books) multiple citations; and U.S. Pat. Nos. 4,640,286 and 4,803,988.

Based upon the foregoing, it has been found that biphasic pulses can be utilized to good advantage to enhance the therapeutic benefit of electrical stimulation, and, more particularly, to suppress pain. The important factors and their apparent result for pain reduction are as follows:

1) A positive pulse applied through a first electrode to the nerve fibers sets the nerve fibers into a condition similar to the refractory period (this pulse is important because it apparently causes a large number of nerve fibers to be synchronized at the same time into the same state or period, thereby causing them to return to the hyperexcitability condition simultaneously);

2) A negative pulse thereafter applied through the first electrode to the nerve preferably 1.8 milliseconds (ms) later (range of about 1.7 ms to about 2.0 ms) excites the nerve fibers (a negative pulse has been found to provide better stimulation of the action potential, and the negative pulse is timed to arrive just as the nerve fibers leave the refractory period so that the time interval between the pulses of the pulse pair is therefore the same as the time interval of the refractory period—if applied apparently earlier or later, fewer nerve fibers are excited because they are either in the relative refractory period, or beyond, and, therefore, are harder to excite);

3) Inverting of the negative pulse to a positive pulse and applying the resulting positive pulse through the second electrode (i.e., the second electrode receives the mirror image of the waveform applied to the first electrode) to the nerve fibers results in a pulse suitable to set the nerve fibers in the same manner as above described for the positive pulse applied through the first electrode;

4) Inverting of the positive pulse of the next occurring pulse pair and applying the resulting negative pulse to the nerve fiber results in a pulse suitable to excite the nerve fibers in the same manner as described above for the negative pulse applied through the first electrode since this pulse occurs 1.8 ms (range of about 1.7 ms to 2.0 ms) after the preceding applied positive pulse through the second electrode;

5) Application of the next occurring positive pulse, applied to the nerve fibers after a time period following application of biphased pulses of positive are then negative polarity, which time period is based upon the time of peak relative excitability (i.e. a time period equal to the known time between the action potential and the maximum hyperexcitability condition of the nerve fibers to be stimulated), again sets the nerve fibers; and 6) The width of the pulses is maximized at about 60 microseconds (range of about 50 microseconds to about 70 microseconds) with the pulse shape or waveform (for example, rise time and or fall time) being not as important, and pulse amplitude and duration being preferably the same for both the positive and negative pulses of each pulse pair.

A digital embodiment 10 of apparatus useful for delivering current by means of biphasic pulses is shown in FIG. 1. As shown, crystal 12 is utilized as a part of crystal oscillator 14 to provide output clock pulses. These pulses are coupled through digital counter 16 which produces a plurality of outputs, as desired, which are coupled through decoding logic unit 18 (which could also be a ROM unit) to provide a plurality of identical waveforms each of which includes timewise spaced pulses with the corresponding pulses of each waveform being offset with respect to one another, as indicated in FIG. 2.

As indicated in FIG. 1, outputs $\phi A1$ and $\phi A2$ are applied to output driver 20 for a first channel (channel A), while outputs $\phi B1$ and $\phi B2$ are applied to output driver 22 for a second channel (channel B). It is to be realized, however, that a single channel could be utilized, if desired.

At output driver 20, the pulses of output $\phi A2$ are inverted with respect to those of output $\phi A1$ (as can be achieved by connecting the output to opposite sides of a transformer or, as is preferred, connecting the $\phi A2$ output through an inverting amplifier) so that the output coupled from output driver 20 includes biphased current pulses as indicated in FIG. 3 (Channel A).

While not specifically illustrated, it is to be realized that while one electrode connected to output driver 20 (an electrode connected to the positive output for Channel A, for example) receives pulses as illustrated in FIG. 3 (Channel A), the other electrode connected to output driver 20 (an electrode connected to the negative output for Channel A, for example) will receive an inverted polarity, or mirror image, of the waveform received at the other electrode (i.e., when the electrode connected to the positive output receives a positive pulse the electrode connected to the negative output receives a negative pulse and when the electrode connected to the positive output receives a negative pulse the electrode connected to the positive output receives a positive pulse).

In like manner, the pulses of output $\phi B2$ are inverted with respect to those of output $\phi B1$ so that the output from output driver 22 includes biphased pulses (as indicated in FIG. 3(Channel B), with the pulses applied to the separate electrodes (connected with different ones of the positive and negative outputs) are inverted in polarity with respect to one another in the same manner as described above with respect to the channel A outputs. In addition, as indicated in FIG. 3, the pulses at channel B are preferably timewise offset with respect to the comparable pulses at channel A, as is necessary to achieve isolation between channels.

As indicated in FIGS. 2 and 3, the pulses are illustrated spaced 1.8 ms from one another. This spacing, as brought out above, has been found to be preferable for pain reduction (as is the object, for example, when using conventional transcutaneous nerve stimulating (TENS) devices).

Thus, by applying a positive pulse to a first electrode and then applying a negative pulse to the first electrode at a later time corresponding to the known refractory time for the nerve fibers to be stimulated (i.e., 1.8 ms for pain reduction), and inverting the negative pulse to a positive pulse which is applied through a second electrode and then inverting a later occurring positive pulse to a negative pulse which is also applied through the second electrode at a time corresponding to the known refractory time for the nerve fibers to be stimulated (i.e., 1.8 ms for pain reduction), stimulation of the nerve fibers is enhanced since both electrodes are thus made active and the time of application is within the excitability period (i.e., occurs at a time less than the timewise occurrence of the enhanced excitability condition of the nerve fibers to be stimulated).

As can be appreciated, through use of a symmetrical waveform in which all pulses are timewise equally spaced from one another, this results in delivering a substantially net zero DC charge to the user.

Often, however, it is important, and/or desirable, that body treatment be effected as well as pain suppression. It is known, for example, that a negative DC is useful for reducing edema, and that a negative DC applied to a wound (often in conjunction with positive DC) is useful in wound healing.

While such negative DC might be applied by means of negative pulses or a constant negative current, it has been found that a net negative DC charge can also be applied by use of biphasic pulses similar to the biphasic pulses above set forth. Particularly advantageous biphasic pulses found useful are described in U.S. Pat. No. 4,803,988, which patent is hereby incorporated by reference herein.

As brought out in this patent, biphasic pulses with a greater number of negative pulses (or a greater number of positive pulses, if needed) can be generated and applied through equally active electrodes, and this results not only in enhancing pain suppression but also provides a net DC charge.

Apparatus for generating such pulses is shown in U.S. Pat. No. 4,803,988 and, as brought out in U.S. Pat. No. 4,803,988, dual electrodes can be made substantially equally active by generating a waveform, as typically shown in FIG. 4A (Channel A) of the drawings included in this application, and applying this waveform to one electrode, with the mirror, or inverted, image of this waveform, as typically shown in FIG. 4B (Channel B), being applied to the other electrode. If the apparatus shown in U.S. Pat. No. 4,803,988 is utilized, then the apparatus must utilize coupling allowing delivery of the DC component, such as, for example, direct coupling, rather than transformer coupling, as shown, in order to provide a net DC charge, as is necessary in this invention.

As indicated in FIG. 4 (Channel A), the first pulse (a positive pulse) is applied to a first electrode to set the nerve fibers, and a second pulse (a negative pulse) is later applied to the first electrode after a time period substantially equal to that of the known refractory period to excite the nerve fibers (the illustration of FIG. 4 illustrates optimization for pain so that the spacing between the first and second electrodes is about 1.8 milliseconds with the next positive pulse then occurring at a time based upon the enhanced excitability condition of the nerve fibers to be stimulated—for pain, the maximum hyperexcitability condition occurs about 4.5 ms after the applied positive pulse).

As indicated in FIG. 4 (Channel B), the second electrode of a dual electrode pair will have applied thereto the mirror, or inverted, waveform of that applied to a working electrode, and therefore will have a negative pulse applied when the first electrode, has a positive pulse applied thereto. This applied negative pulse does not set the nerve fibers through the second electrode (and hence no later occurring inverted and applied negative pulse will excite the nerve fibers).

However, a negative pulse that occurs later is inverted to a positive pulse to set the nerve fibers so that a later inverted and applied negative pulse can excite the nerve fibers. Specifically, as shown in FIG. 4, by inserting a second negative pulse (spaced about 0.9 ms from the first negative pulse for pain as indicated in FIG. 4 (Channel A), the inverted waveform applied to the second electrode causes the resulting second positive pulse to set the nerve fibers so that a later occurring negative pulse (i.e., the inverted positive pulse occurring during the next succeeding pulse group occurrence, as shown in FIG. 4A (Channel A) excites the nerve fibers at the second electrode if the pulse spacing therebetween is made substantially equal to the known refractory period (i.e., 1.8 ms for pain, as indicated in FIG. 4 (Channel B).

While the second negative pulse inserted closely adjacent to the first negative pulse in the waveform shown in FIG. 4 (Channel A) does not adversely affect performance of the pulses applied to the first electrode (after a nerve fires, the nerve ignores pulses for an interval thereafter as brought out above), this pulse does provide proper spacing for optimizing stimulation under the second electrode (both as to spacing of the pulses and the repetitive occurrences of the pulse groups) so that the result is that both electrodes are made substantially equally active.

By use of a combination of apparatus above-described, a combination of pulses can be produced that is useful for both body treatment (i.e., for treating edema and/or a wound, for example) and for pain suppression.

Apparatus 24 for providing a combined, or multiplexed, waveform useful for body treatment and pain suppression is shown in FIG. 5. As shown, a microprocessor 26, with control inputs 28 including provision for causing conventional variations such as for varying intensity, is utilized to produce outputs to positive and negative pulse drivers 30 and 32, which drivers are connected to electrodes 34 and 36.

As can be appreciated, microprocessor 26 is preferably programmed to provide pulse outputs equivalent to those indicated in FIGS. 3 and 4 as a combined output such as shown in FIG. 6. Control of waveform duration variations is also preferably provided as a part of control inputs 28 for establishing the parameters for occurrence of each segment of the pulse train, as brought out more fully hereinafter. In addition, a mode selector is also preferably provided as a part of control inputs 28 for selecting between operational modes, as brought out more fully hereinafter.

While not specifically shown, it is to be appreciated that a generating unit such as shown in U.S. Pat. No. 4,803,988 (or any conventional generator producing negative pulses) could be utilized to produce a net DC charge and a generating unit such as that shown in FIG. 1 could be utilized to produce a net zero DC charge, with the control input being a timing control to establish the duration of occurrence of pulses from each generating unit.

The apparatus and method of this invention is particularly useful when body treatment and pain suppression are both needed. This occurs, for example, after an operation when it is necessary to both relieve both pain and reduce edema.

Through use of the current waveform shown in FIG. 4, DC charge is delivered to the tissue (using apparatus that is discussed in U.S. Pat. No. 4,803,988, this could be, for example, at a rate of about 222 60-microsecond phases per second). When the current waveform, as shown in FIG. 3, is utilized, there is no DC delivered.

In spite of this difference, when both waveforms are successively applied to a subject, or user, they feel the same. When the waveform delivering DC charge is first produced, there is a barely perceptible sharp sensation under the positive electrode, but this passes in a few seconds. Then, when the waveform delivering no DC charge is produced (with the waveform delivering DC charge being no longer produced), there is no perception of change.

Thus, by applying a proper waveform containing DC in one segment alternately with a waveform that has no DC component in a second segment, both body treatment and pain suppression can be effected. Through use of an algorithm that controls the duty cycle, or proportioning, of the two segments of the waveform, the DC charge can be maintained constant even though changes, within establishable limits, occur in the pulses of the waveform.

It is thus possible, using this invention, to raise (or lower) the intensity and, by varying the period that the AC containing waveform (i.e., net zero DC charge segment) is on relative to the period that the DC containing waveform is on, maintain the DC constant. Charge delivered to the tissue thus remains constant. This makes it possible for the DC content to be specified independent of the amplitude and the patient may set the amplitude to any level desired for comfort. This avoids the use of standard intensity levels that cannot be tolerated by all patients, while insuring that all patients get the prescribed DC treatment.

Referring again to FIG. 4, it can be shown that this waveform delivers about 0.024 coulombs of charge for every milliampere of current intensity in a 30 minute treatment. For post-op use, it now appears best to provide two operating modes. When the treatment is begun, it is desirable, during a first operational mode, to charge the tissue with a relatively large dose of ions to reduce edema and begin the healing effect. Then, after the tissue has been charged, the apparatus is switched to the second operational mode wherein the apparatus will continue to stimulate the nerves as before, but with a very low DC dose just sufficient to maintain the DC polarity while the stimulation continues non-stop (normally for two or more days).

During the initial large dose phase (i.e., during the first operative mode), the DC might be delivered, for example, over a ½ hour period. Assuming that this amounts (typically) to 20 seconds of DC waveform for every 10 seconds of AC waveform at a 35 milliampere (peak) intensity, if the intensity were reduced to 23 milliamperes (peak), the DC would have to be on 100% of the time. If the intensity were increased, on the other hand, to 42 milliamperes (peak), the DC would be on 17 seconds and the AC would be on 13 seconds.

In the DC maintenance mode (second operative mode), the DC is delivered at a low rate so that over a 24-hour period, the patients receive just as much DC as if they had two 30-minute high rate treatments.

In the present preferred embodiment, the DC algorithm is oriented around a fixed increment of interval of DC treatment, for example, one second of waveform shown in FIG. 4. This is followed by a variable number of seconds of AC waveform shown in FIG. 3 so that the average DC delivered will be constant. For example, using 30 minute treatment times as a starting point, and using one second of DC wave at 35 milliamperes (peak), apparatus according to this invention could deliver the DC equivalent of two ½-hour treatments in 40 minutes. Relative to a whole day, this is:

$$\frac{\frac{2}{3} \text{ hour/day DC waveform ON}}{23\frac{1}{3} \text{ hours/day OFF DC off}} = \frac{1}{35 \, ma}$$

Thirty-five milliamperes peak is a typical strong comfortable level for the post-op waveform using 3 inch square electrodes.

If the intensity were to increase to 70 milliamperes (peak), then the need for DC intervals would drop to half as often. This implies a ratio of 70 to 1.

If the intensity were turned down to half, or 17.5 milliamperes (peak), then the DC must be on twice as long to compensate. This would be 17.5 seconds AC wave (FIG. 3) to 1 second DC wave (FIG. 4). Generally for a specific DC charge level, the AC wave time in seconds equals the intensity in milliamperes, or in general, $$AC \text{ wavetime} = \text{Current Intensity} \times K.$$

where K is inversely proportional to the desired total DC treatment charge per day.

FIG. 7 sets forth the microprocessor algorithm to illustrate use of the apparatus of this invention as a post-op unit for body treatment and pain suppression. The area of the electrode or charge density is read in since DC treatment dose depends primarily on the area of the electrode, and this input can be from controls, EEPROM data, fixed ROM, coded electrode connectors, or other means. The mode switch is read to determined high or low DC dose mode with the high DC charge dose being equal to a large segment of DC time with a relatively short AC time segment (the unit could also be programmed to give a high dose treatment automatically on initial turn-on). Continuing treatment normally requires a short DC time segment with a relatively long AC time segment.

In summary, a post-op TENS according to this invention uses two waveforms that are combined and operated in two different modes. In the loading dose mode (first operational mode), the DC level is high so that the patient receives a large dose of DC (equivalent to a wound healing treatment for 30 minutes at a peak intensity of 35 ma). In the continuous mode (second operational mode), the waveform is primarily the AC waveform shown in FIG. 3 for pain relief, but about 3% of the time the DC waveform shown in FIG. 4 is applied to maintain DC charge in the tissue without the overdose that could occur if a high rate of purely DC pulses, for example, was applied continuously. Using the combined waveform shown in FIG. 6, the patient is unaware that the segments of the combined waveform are different and that different effects produced therefrom are occurring.

For wound healing, it has been found undesirable to treat continuously. Normally, pain relief is not an important objective. In wound healing, it has been found that treatments may be given twice a day for one half hour using high DC doses (as set forth in U.S. Pat. Application Ser. No. 07/103,696, issued July 11, 1989 as U.S. Pat. No. 4,846,181, above referenced).

FIG. 8 is a DC charge regulation algorithm illustrating use of the apparatus of this invention as a dual waveform, wound healing stimulator. This stimulator is preferably programmed by an external computer. While programming the stimulator, the clinician specifies charge per ½ hour treatment. The clinician can specify, for example, any value up to 0.65 coulombs/30-minute treatment. The value of the charge is primarily proportional to the area of the treatment electrode.

The master computer program uses the charge to calculate the minimum peak current needed to deliver the prescribed charge.

$$\text{Minimum peak current} = \frac{\text{(prescribed charge)}}{.024 \text{ coulombs}/ma/30 \text{ minutes}}$$

These data are transmitted to the stimulator where they are stored, such as in an EEPROM. The stimulator program, outlined in FIG. 8, shows the algorithm used to produce the multiplexed AC/DC waveforms. During program initialization, the EEPROM protocol is read and the treatment parameters are set up. At this time the DC on-time in seconds is calculated from the DC charge value (DC charge per treatment is given in coulombs/half hour treatment and typical values might range from 0.2 to 0.6 coulombs, depending upon the size of the electrode). The DC on-time is not critical. A simple practical value would be:

DC ON-TIME = DC CHARGE × 40.

where 40 is an arbitrary constant that produces AC ON-TIMES with a minimum of computational rounding error.

An even simpler algorithm is:
For DC charge 0.26 to 0.65 coulombs, DC ON-TIME = 10 seconds
For DC charge 0.26 to 0.65 Coulombs, DC ON-TIME = 20 seconds For DC charge is given in the protocol as "Q" followed by three ascii numbers (with no decimal point since the decimal point is assumed to precede the numbers). If the data doesn't fit this, the incomplete protocol flag is set and treatment is not allowed.

After the program has entered the main program loop, the most important part of the algorithm is where the AC ON-TIME is calculated using the current amplitude (set by the patient) and the DC ON-TIME. For large DC charge doses, the DC waveform is on proportionally longer. For example, for 0.564 coulombs/30 minutes, the DC waveform is on for 20 seconds, then the AC waveform is on for variable lengths of time, inversely proportional to the pulse amplitude selected by the patient. The minimum amplitude level sufficient to deliver charge specified in the protocol is the minimum necessary to deliver the prescribed DC charge, and in the program, the variable INTENSACT, or present intensity is initialized equal to the level in the protocol. Every time the patient, or user, changes the amplitude, the AC ON-TIME is recalculated according to the formula:

AC ON-TIME = DC ON-TIME ((amplitude ×

CHARGE RATE/DC CHARGE) − 1).

When DC ON-TIME is determined by initialization and is proportional to total DC charge/treatment, where AC ON-TIME = the time in seconds during which the AC waveform is on.

AMPLITUDE = the current intensity in milliamperes set by the patient.

DC CHARGE = is the amount of DC in coulombs prescribed in the treatment protocol.

CHARGE RATE = a constant, the amount of charge per milliampere of current for the DC waveform, for example, 0.024 coul/ma/30 minutes.

The total waveform cycle time is the sum of the DC ON-TIME and the AC ON-TIME. A flag called "DC" (resulting from setting of a wave which is a variable that is counted down to zero, one count each second) tells the pulse generation interrupt whether to generate AC or DC waveforms, and the DC flag ensures that the cycle starts with the DC waveform. The timer module in the main loop is consulted once per second and a value, "WAVE" set equal to the cycle time is decremented to determine when the waveforms should change (the timer module not only calculates the proportion of AC waveform to DC waveform, but also controls the total treatment time and other timed functions such as sounding wake-up alarm, and a treatment complete alarm).

In the stimulation module, the amplitude actually used by the D-to-A converter (in microprocessor 26) is calculated and stored in the output port. When stimulation is turned on (stimulation is activated by pressing a stimulation button in the switch matrix to set the STIM request flag), the program automatically increments the current up to the minimum current intensity required to produce the prescribed DC treatment. This is well below the sensory threshold with standard electrodes. The patient uses the amplitude control (pulse variations control inputs 28) to increase the level to a strong, comfortable setting. As the intensity goes up, the AC ON-TIME increases to hold the charge constant. The actual AC and DC waveforms are generated by a pulse interrupt routine that uses the DC flag to determine which waveform is produced.

While one set of positive and negative (biphasic) pulse drivers 30 and 32 are shown in FIG. 5, it is to be appreciated that two sets of biphasic drivers could be utilized for dual channels with a pair of electrodes 34 and 36 used with each channel. In addition, when dual channels are utilized, electrodes 36 can be replaced by one common return electrode.

As can be appreciated from the foregoing, this invention provides an apparatus and method enabling both body treatment and pain suppression to be effected through use of a combined waveform that stimulates both body tissue and nerve fibers with provisions being made to allow the intensity level causing nerve fiber stimulation to be varied while maintaining a constant body tissue stimulating DC charge.

What is claimed is:

1. Medical apparatus, comprising:
   generating means for generating an electrical output signal having a continuous series of first and second time-wise spaced segments, said first segment including an AC signal that provides AC and a net DC charge derived from said AC signal so that said first segment is suitable both for nerve fiber stimulation and for body tissue stimulation with said AC having a direct effect to cause suppression of pain and with said net DC charge having a direct effect to cause at least one of edema reduction and wound healing, and said second segment including AC with substantially zero DC charge so that said second segment is suitable for nerve fiber stimulation with said AC with said substantially zero DC charge having a direct effect to cause suppression of pain; and application means connected with said generating means for coupling said output signal to the body of a user to thereby utilize said first segment for suppression of pain and at least one of edema reduction and wound healing, and to thereby utilize said second segment for suppression of pain.

2. The apparatus of claim 1 wherein said generating means includes a microprocessor.

3. The apparatus of claim 1 wherein said generating means produces said output signals on pulses, wherein said pulses of said first segment include a greater number of pulses of negative or positive polarity, and wherein said pulses of said second segment include an equal number of pulses of each polarity.

4. The apparatus of claim 1 wherein said generating means causes said first segment of said output signals to provide a net negative DC charge.

5. The apparatus of claim 1 wherein said application means includes electrode means for noninvasively engaging the skin of a user to couple said output signals from said apparatus to the user.

6. Medical apparatus, comprising:

generating means for generating output signals having first and second segments, said first segment providing a net DC charge suitable for body tissue stimulation with said net DC charge having a direct effect of itself to cause at least one of edema reduction and wound healing, and said second segment providing a substantially zero DC charge suitable for nerve fiber stimulation to cause suppression of pain;

application means connected with said generating means for coupling said output signals to a user for causing said at least one of edema reduction and wound healing and said suppression of pain; and control means for causing said generating means to vary at least said second segment of said output signals to thereby vary the level of pain suppression, said control means also causing said generating means to adjust said first segment to maintain said DC charge substantially constant despite variations in the level of pain suppression.

7. Medical apparatus, comprising:

generating means for generating electrical output signals having a continuous series of first and second time-wise spaced segments, said first segment including biphasic pulses providing an DC signal that has AC and a net DC charge derived from said biphasic pulses so that said biphasic pulses are suitable for both nerve fiber stimulation and for body tissue stimulation, and said second segment including biphasic pulses providing a substantially zero DC charge so that said biphasic pulses are suitable for nerve fiber stimulation;

control means for controlling said generating means whereby at least the pulses of said second segment can be varied; and application means connected with said generating means for coupling said output signals to the body of a user whereby said first segment is utilized both for suppression of pain and for at least one of edema reduction and wound treatment, and said second segment is utilized for suppression of pain.

8. The apparatus of claim 7 wherein said generating means causes said first segment to have a greater number of negative pulses than positive pulses whereby a net negative DC charge is provided through said first segment to said application means.

9. Medical apparatus, comprising:

generating means for generating output signals having first and second segments, said first segment including biphasic pulses providing a net DC charge; and said second segment including biphasic pulses providing a substantially zero Dc charge;

control means for controlling said generating means, said control means including means for controlling at least the intensity of the pulses of said second segment whereby said intensity can be varied, and said control means also including means for maintaining said net DC charge substantially constant regardless of said changes of pulse intensity; and application means connected with said generating means for coupling said output signals to a user whereby said first segment is utilized at least for wound treatment and said second segment is utilized for suppression of pain.

10. Medical apparatus, comprising:

generating means for generating output signals having first and second segments, said first segment including biphasic pulses providing a net DC charge, and said second segment including biphasic pulses providing a substantially zero DC charge;

control means for controlling said generating means whereby at least the pulses of said second segment can be varied;

application means connected with said generating means for coupling said output signals to a user whereby said first segment is utilized at least for wound treatment and said second segment is utilized for suppression of pain; and mode means for establishing first and second operating modes such that when said apparatus is in said first operating mode said generating means is caused to provide a large net DC charge to be coupled to a user, and such that when in said second operating mode said generating means is caused to provide a net DC charge to be coupled to a user that is less than that provided by said apparatus when in said first operating mode.

11. A method for electrical stimulation and treatment of a user for therapeutic purposes, said method comprising:

providing an output signal having first and second segments with said first segment including biphasic pulses providing a net DC charge and said second segment including biphasic pulses providing a substantially zero DC charge;

applying said first and second segments to a user whereby said first segment is utilized for wound treatment and said second segment is utilized for suppression of pain; and controlling said pulses of said segments so that said net DC charge is maintained substantially constant.

12. The method of claim 11 wherein said method includes generating a greater number of negative pulses than positive pulses at said first segment to thereby produce a net negative DC charge.

13. The method of claim 11 wherein said method includes varying at least the pulse intensity of at least said second segment to thereby adjust the level of pain suppression, and maintaining said net DC charge substantially constant regardless of said variations of pulse intensity.

14. The method of claim 11 wherein said method includes establishing first and second operating modes, causing, when in said first operating mode, said first segment of said output signal to provide a high DC charge to be applied to a user, and causing, when in said second operating mode, said first segment of said output signal to provide a DC charge to be applied to a user that is less than that provided when in said first operating mode that would cause an overdose of DC to be delivered to said user when operated continuously.

15. The method of claim 11 wherein said method includes varying the intensity of said pulses of said second segment, and wherein said net DC charge is maintained substantially constant by varying the duration of application of said first segment relative to said second segment when the intensity of said pulses of said second segment is varied.

16. A method for electrical stimulation and treatment of a user for therapeutic purposes, said method comprising:
providing an output signal having a continuous series of first and second time-wise spaced electrical signal segment, said first electrical signal segment including a plurality of first pulses providing an AC signal that has AC and a net DC charge derived from said plurality of first pulses so that said first electrical signal segment is suitable both for nerve fiber stimulation and for body tissue stimulation with said first plurality of pulses providing said net DC charge having a direct effect to cause suppression of pain and at least one of edema reduction and wound healing, and said second electrical signal segment including a second plurality of pulses providing a substantially zero DC charge so that said second electrical signal segment is suitable for nerve fiber stimulation to cause suppression of pain; and
applying said first and second electrical signal segments of said output signal to a user to thereby utilize said first electrical signal segment for suppression of pain and at least one of edema reduction and wound healing, and to thereby utilize said second electrical signal segment for suppression of pain.

17. The method of claim 16 wherein said method includes providing a net negative DC charge suitable for at least one of wound treatment and edema reduction.

18. The method of claim 16 wherein said first and second electrical signal segments include biphasic pulses.

19. A method for electrical stimulation and treatment of a user for therapeutic purposes, said method comprising:
providing a first electrical signal segment having a net DC charge suitable for at least body tissue stimulation with said net DC charge having a direct effect of itself to cause at least one of edema reduction and wound healing;
providing a second electrical signal segment having a substantially zero DC charge suitable for nerve fiber stimulation to cause suppression of pain;
controlling each segment whereby the net DC charge is maintained substantially constant regardless of level variations of at least said second segment; and
applying said first and second electrical signal segments to a user for causing said at least one of edema reduction and wound healing and said suppression of pain.

* * * * *

UNITED STATES PATENT AND TRADEMARK OFFICE
CERTIFICATE OF CORRECTION

PATENT NO.  : 5,117,826
DATED       : June 2, 1992
INVENTOR(S) : Bartelt, et al.

It is certified that error appears in the above-identified patent and that said Letters Patent is hereby corrected as shown below:

Column 13, line 58, "DC" should be --AC--.

Signed and Sealed this

Thirty-first Day of August, 1993

*Attest:*

BRUCE LEHMAN

*Attesting Officer*      *Commissioner of Patents and Trademarks*